United States Patent [19]
Hosoi

[11] Patent Number: 5,980,042
[45] Date of Patent: Nov. 9, 1999

[54] EYE REFRACTIVE POWER MEASUREMENT APPARATUS

[75] Inventor: Yoshinobu Hosoi, Gamagori, Japan

[73] Assignee: Nidek Co., Ltd., Japan

[21] Appl. No.: 09/185,704

[22] Filed: Nov. 4, 1998

[30] Foreign Application Priority Data

Nov. 5, 1997 [JP] Japan ................................. 9-320416

[51] Int. Cl.⁶ .................................................. A61B 3/10
[52] U.S. Cl. .................................................... 351/212
[58] Field of Search .................. 351/204, 205, 351/206, 211, 212, 246, 247

[56] References Cited

U.S. PATENT DOCUMENTS 5,406,076  4/1995  Mimura et al. ................... 250/229
5,500,697  3/1996  Fujieda ............................ 351/212
5,684,562  11/1997 Fujieda ............................ 351/212

FOREIGN PATENT DOCUMENTS 59-91943  5/1984  Japan .

Primary Examiner—George Manuel
Attorney, Agent, or Firm—Finnegan, Henderson, Farabow Garrett & Dunner, L.L.P.

[57] ABSTRACT

An eye refractive power measurement apparatus including a refractive power measurement device for objectively measuring a refractive power of an eye to be examined based on reflected light from a fundus of the eye, the apparatus comprising a pupil detecting device for detecting a pupil size upon measuring the refractive power of the eye by the refractive power measurement device, a memory device for storing plurality of refractive power measurement results obtained by the measurement device and pupil detection results obtained by the pupil detecting device in correspondence therebetween, a typical value determination device for determining a typical value of the refractive power based on the refractive power measurement results and the pupil detection results stored in the memory device and an output device for outputting the typical value determined by the typical value determination device.

12 Claims, 4 Drawing Sheets

EYE REFRACTIVE POWER MEASUREMENT APPARATUS

BACKGROUND OF THE INVENTION

1. Field of the Invention

The present invention relates to an eye refractive power measurement apparatus which objectively measures a refractive power of an eye to be examined.

2. Description of Related Art

It is conventionally known an eye refractive power measurement apparatus which projects a target for measurement onto a fundus of an eye to be examined and objectively measures a refractive power of the eye based on reflected light therefrom. When precisely measuring a refractive power of the eye using this kind of apparatus, the measurement is carried out usually by making the accommodation of the eye relaxed by a fogging mechanism and the measurement is repeated a plurality of times. Statistical processes are given to the measurement results obtained thereby such as letting the median or the average be the typical value of the all data values indicating the eye refractive power. The value obtained through the statistical processes is utilized as an initial value in a subjective measurement to be performed next.

However, in a measurement with this kind of apparatus, an examinee looks into the apparatus, which is likely to cause so-called instrumental myopia. Thus, the typical value decided in the aforementioned way may not be the value obtained in a condition where the accommodation of the eye is fully relaxed. Especially in the case of examining an eye which has low hyperopia, accommodation of the eye tends to be unstable.

SUMMARY OF THE INVENTION

The present invention has been made in view of the above circumstances and has an object to overcome the above problems and to provide an eye refractive power measurement apparatus which is able to obtain a highly reliable typical value from plurality of measurement results with accuracy.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly de scribed herein, an eye refractive power measurement apparatus including refractive power measurement means for objectively measuring a refractive power of an eye to be examined based on reflected light from a fundus of the eye, the apparatus comprises pupil detecting means for detecting a pupil size upon measuring the refractive power of the eye by the refractive power measurement means, memory means for storing plurality of refractive power measurement results obtained by the measurement means and pupil detection results obtained by the pupil detecting means in correspondence therebetween, typical value determination means for determining a typical value of the refractive power based on the refractive power measurement results and the pupil detection results stored in the memory means and output means for outputting the typical value determined by the typical value determination means.

In another aspect of the present invention, an eye refractive power measurement apparatus comprises refractive power measurement means for objectively measuring a refractive power of an eye to be examined based on reflected light from a fundus of the eye, pupil detecting means for detecting a pupil size upon measuring the refractive power of the eye by the refractive power measurement means, memory means for storing plurality of refractive power measurement results obtained by the measurement means and pupil detection results obtained by the pupil detecting means in correspondence therebetween, judging means for judging whether or not the eye possibly has low hyperopia based on the pupil detection results stored in the memory means and display means for displaying a judgment result made by the judging means.

Further in another aspect of the present invention, an eye refractive power measurement apparatus comprises refractive power measurement means for objectively measuring a refractive power of an eye to be examined based on reflected light from a fundus of the eye, pupil detecting means for detecting a pupil size upon measuring the refractive power of the eye by the refractive power measurement means, memory means for storing plurality of refractive power measurement results obtained by the measurement means and pupil detection results obtained by the pupil detecting means in correspondence therebetween, eliminating means for eliminating refractive power measurement results corresponding to pupil detection results in which the pupil size is smaller than a predetermined pupil size from the refractive power measurement results stored in the memory means, typical value determination means for determining a typical value of the refractive power based on refractive power measurement results exclusive of the refractive power measurement results eliminated by the eliminating means and output means for outputting the typical value determined by the typical value determination means.

As has been described above, in accordance with the present invention, the value can be obtained with higher accuracy from the plurality of measurement results.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
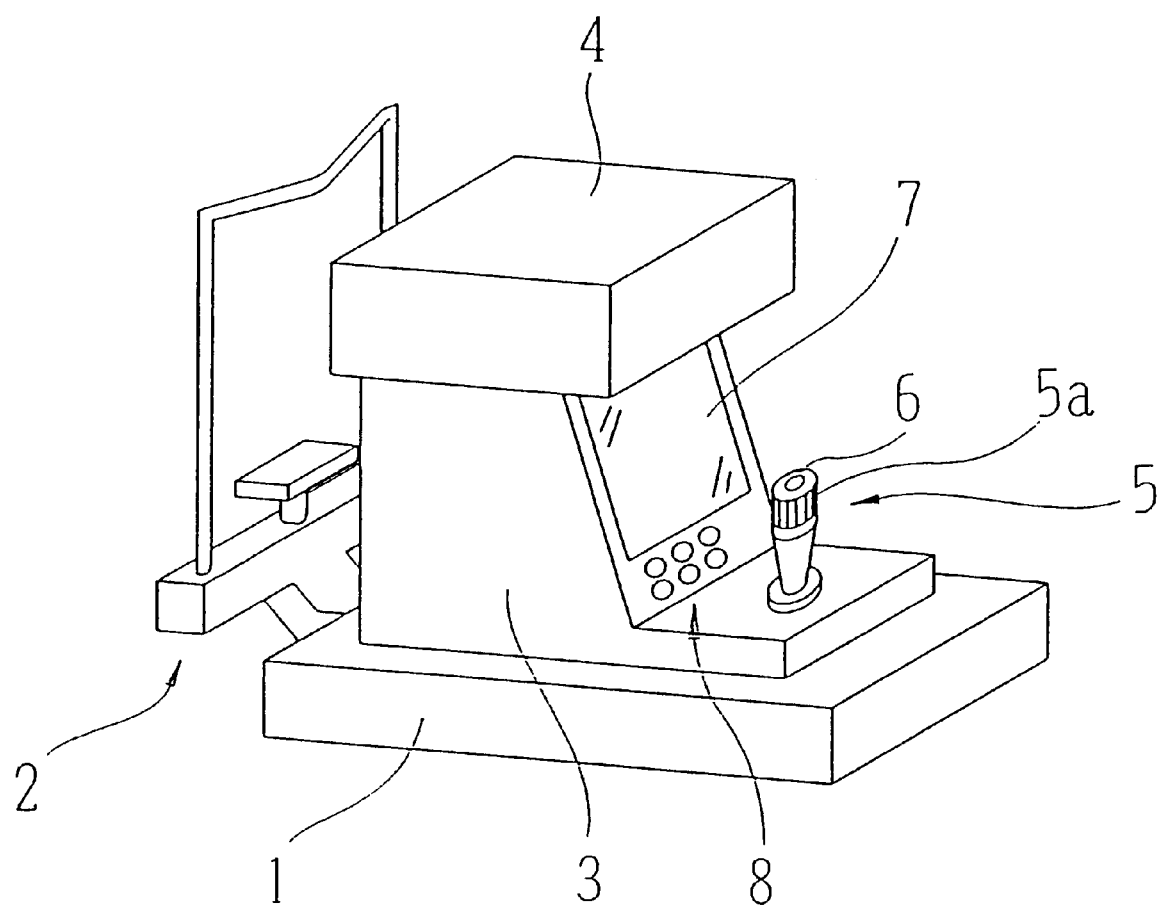
FIG. 1 is an overview of an eye refractive power measurement apparatus of the preferred embodiment of the present invention.

A detailed description of one preferred embodiment of an objective eye refractive power measurement apparatus embodying the present invention will now be given ref erring to the accompanying drawings. FIG. 1 is an overview of the apparatus of the preferred embodiment of the present invention. Reference numeral 1 denotes a base and 2 is a face support unit for supporting an examinee's face. 3 is a body and 4 is a measuring part containing optical systems as hereinafter described. Responding to operations of a joystick 5, the body 3 slides along a horizontal plane of the base 1 in back-and-forth and side-to-side directions. By turning a rotation knob 5a, the measuring part 4 moves in up-and-down directions in relation to the body 3. For the details of this joystick mechanism, see U.S. Pat. No. 5,406,076 which corresponds to Japanese Patent Publication of unexamined patent application No. HEI 6-7292 by the present applicant. The joystick 5 is provided with a measurement starting switch 6 at the top thereof. 7 is a TV monitor to display information such as an image of an anterior part of the eye and the like. 8 is a switch part which includes a print switch and the like.

Figure 2:
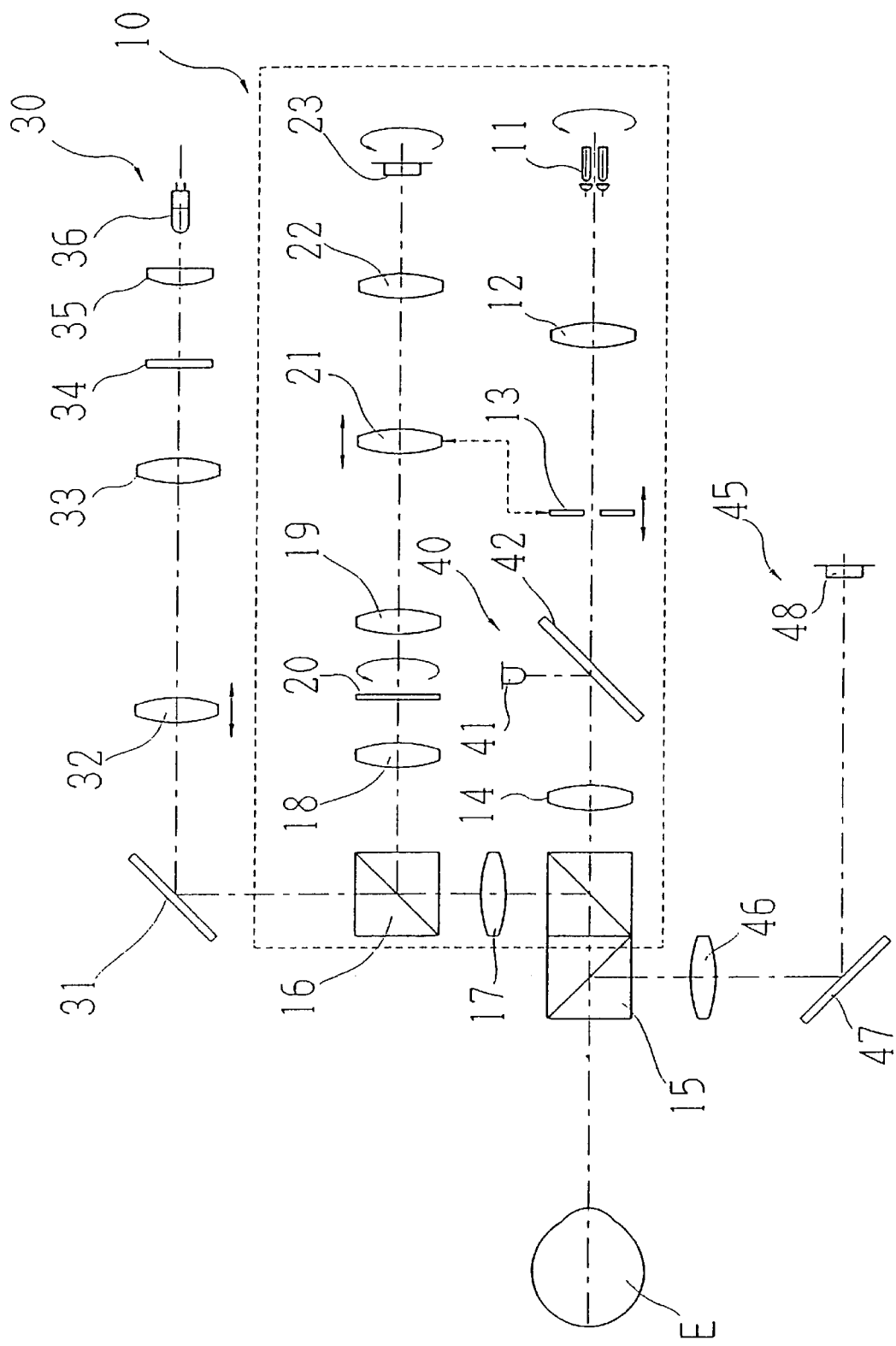
FIG. 2 is a view showing a schematic arrangement of optical systems of the apparatus.

FIG. 2 is a view showing a schematic arrangement of the optical systems of the apparatus. Reference numeral 10 denotes an eye refractive power measuring optical system. 11 is a pair of light sources for measurement which emits measurement light having its wavelength within an infrared range. The light sources 11 are arranged to be rotatable on an optical axis. 12 is a condenser lens. 13 is a target plate for measurement provided with a target for measurement (a spot aperture) thereon. The target plate 13 is movable so as to be moved to a conjugate position with a fundus of the eye E. 14 is a projecting lens, 15 and 16 are beam splitters, 17 is an objective lens, 18 and 19 are relay lenses. 20 is a strip-shaped corneal reflection eliminating mask which is arranged at a conjugate position with a cornea of the eye E to be rotatable on an optical axis. 21 is a movable lens which moves along with the target plate 13. 22 is an image forming lens. 23 is a photo-detector for measurement which rotates about the optical axis being synchronized with the light sources 11 and the corneal reflection eliminating mask 20.

Reference numeral 30 denotes a fixation target optical system. 31 is a mirror. 32 is a first relay lens which moves along an optical axis and thereby fogs the eye E. 33 is a second relay lens, 34 is a fixation target which is arranged at a focal point of the second relay lens 33. 35 is a condenser lens and 36 is an illumination lump.

Reference numeral 40 denotes a target projecting optical system which projects a light bundle to form an image of a target for alignment from a direction of a visual axis. A point light source 41 emits infrared light for projecting a target. The light from the point light source 41 is first reflected by a beam splitter 42 and then passes through the projecting lens 14 thereby made to be parallel to the visual line. The light will be projected from the front of the eye E along the optical axis for measurement so that an image of the target for alignment is formed upon the cornea.

Reference numeral 45 denotes an observation target detection optical system. An image of an anterior part of the eye E illuminated by an unillustrated light source and the image of the target for alignment formed by the target projecting optical system 40 are first reflected by the beam splitter 15, and then photographed by a CCD camera 48 through an object lens 46 and a mirror 47. The CCD camera 48 is also utilized to provide picture signals upon pupil diameter detection, which will be described hereinafter. It is also possible to separately provide an observation optical system and a target detection optical system to detect the target image for alignment which is projected onto the eye E.

Figure 3:
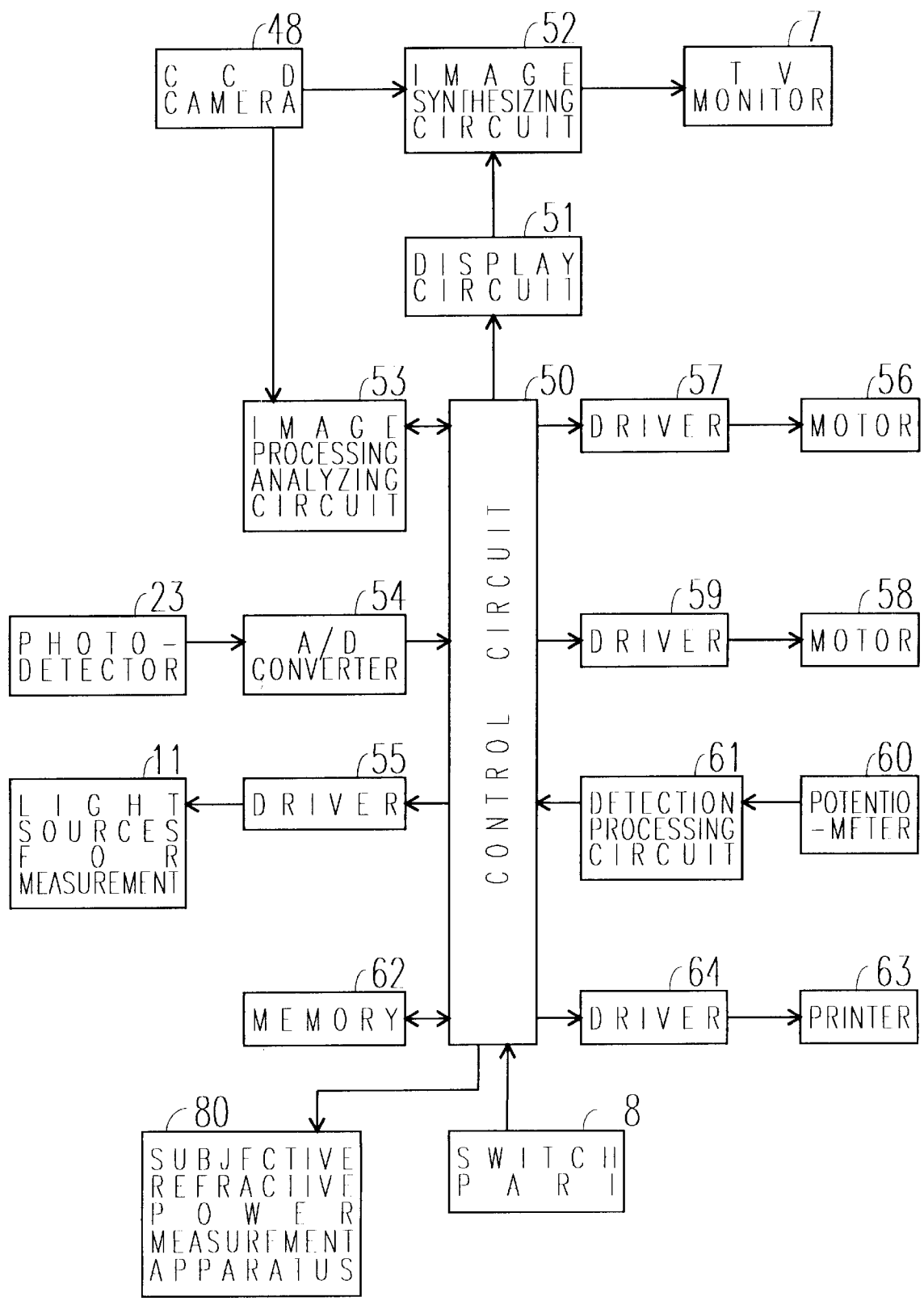
FIG. 3 is a view showing a schematic arrangement of a control system of the apparatus.

FIG. 3 is a view showing a schematic arrangement of the control system of the apparatus. Picture signals from the CCD camera 48 are synthesized in an image synthesizing circuit 52 with signals of characters and graphics which are generated in a display circuit 51 so as to be displayed on the TV monitor 7. The picture signals form the CCD camera 48 is also sent to an image processing analyzing circuit 53 where the pupil diameter detection is carried out. A control circuit 50 for controlling the whole apparatus is connected to an A/D converter 54 which digitizes signals from the photo-detector 23, a driver 55 for the light sources 11, a driver 57 for a motor 56 which rotates the light sources 11, the corneal reflection eliminating mask 20 and the photo-detector 23, a driver 59 for a motor 58 which moves the target plate 13 and the movable lens 21, and the like (although it is not illustrated, each of the divers for the first relay lens 32, the illumination lump 36 and the point light source 41 is likewise connected to the controller 50). 60 is a potentiometer which detects a position of the target plate 13 (the movable lens 21) and 61 is a detection processing circuit for the detection. 62 is a memory to store the measurement result. 63 is a printer and 64 is a driver for the printer 63.

Figure 4:
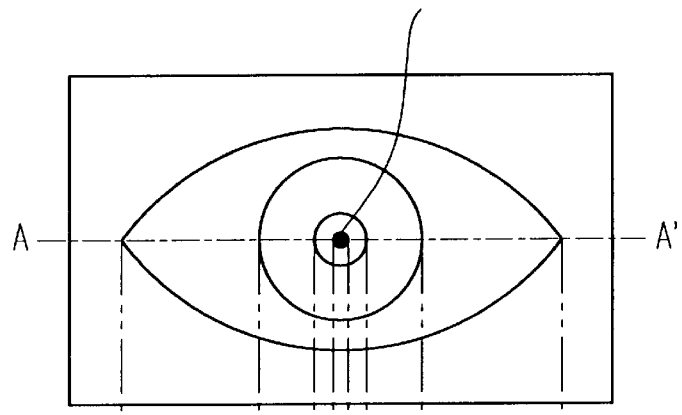
FIGS. 4 (a)–(c) are views showing distribution of light quantity along a line A—A' obtained from the picture signals from a CCD camera.
Figure 4:
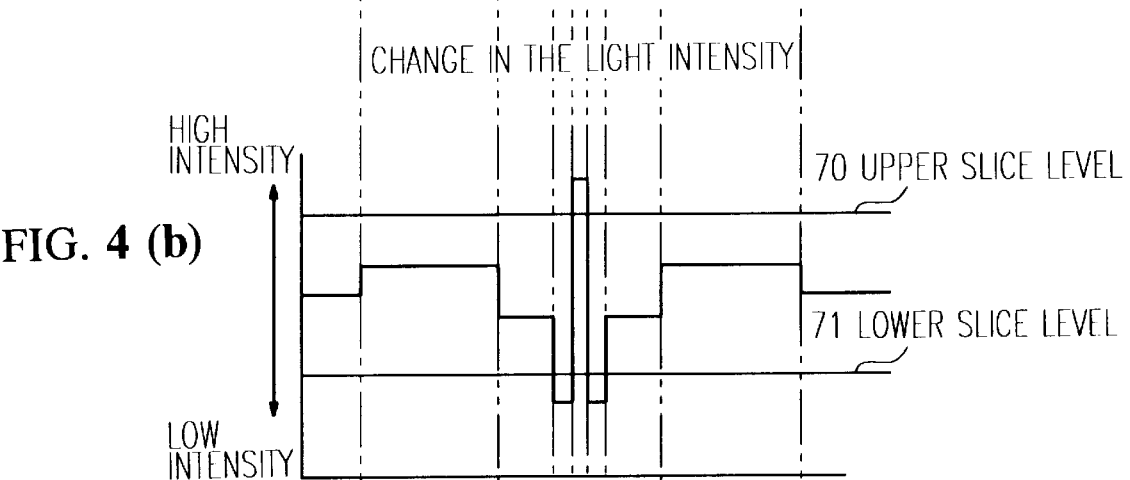
Figure 4:
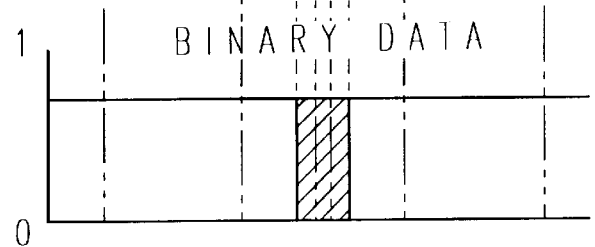

Next, how to detect the pupil size from the image of the anterior part of the eye photographed by the CCD camera 48 will be described. FIG. 4 (a) shows the image of the anterior part of the eye at a completion of the alignment. FIG. 4 (b) shows the distribution of the light quantity received along the scanning line A—A' which intersects the optical axis at a right angle. The light quantity of the image of the anterior part based on the picture signals from the CCD camera 48 differs depending on each part of the image such as the alignment target, the pupil, the iris and the sclera. Therefore, by converting the obtained distribution of the light quantity into binary data using predetermined thresholds, the pupil periphery (edges) on the scanning line A—A' can be obtained so that the pupil diameter can as well be obtained. The picture signals from the CCD camera 48 are first transmitted to the image processing analyzing circuit 53 in which the signals are converted into the distribution of the light quantity as shown in FIG. 4 (b). The distribution of the light quantity is then converted into binary data using two threshold levels, an UPPER SLICE LEVEL 70 and a LOWER SLICE LEVEL 71. To obtain binary data, a part where the light intensity exceeds the UPPER SLICE LEVEL 70 is taken as binary 1, whereas a part where the light intensity is below the UPPER SLICE LEVEL 70 is taken as binary 0. Contrary to the UPPER SLICE LEVEL 70, a part where the light intensity is below the LOWER SLICE LEVEL 71 is taken as binary 1, whereas a part where the light intensity exceeds the LOWER SLICE LEVEL 71 is taken as binary 0. As shown in FIG. 4 (c), the pupil diameter on the scanning line A—A' can be obtained by extracting a range determined as binary 1. In addition, if the above-described operation is repeatedly performed on the scanning lines covering the entire pupil, the pupil area can be obtained.

Furthermore, before executing the measurement, the information about the distribution of the light quantity shown in the FIG. 4 (b) may be displayed on the TV monitor 7, and the examiner may be allowed to set the two thresholds, the UPPER SLICE LEVEL 70 and the LOWER SLICE LEVEL 71 as desired. This arrangement will help to detect the pupil reliably irrespective of changes in the measurement environment (luminous intensity of the surroundings).

Operations of the apparatus having above-described configuration will be explained hereinafter. First, the eye E is to be fixed at a predetermined position with use of the face support unit 2. As observing an image of the anterior part of the eye E displayed on the TV monitor 7, alignments are made by operating the joystick 5 and the rotation knob 5a so as to bring a reticle mark generated in the display circuit 51 and an image of the target for alignment formed by the target projecting optical system 40 into predetermined positions in relation to each other. When the alignment is completed, measurement is to be started at a push of the measurement starting switch 6.

The measurement light emitted from the light sources 11 successively passes through the condenser lens 12, the target plate 13, the beam splitter 42, the projecting lens 14 and the beam splitter 15, then converges in the vicinity of the cornea of the eye E. Thereafter, the measurement light arrives upon the fundus of the eye E thereby projects a target for measurement by the target plate 13 thereon. In case of an emmetropic eye, an image of the target for measurement reflected from the fundus of the eye E is reflected by the beam splitter 15, passes though the object lens 17, reflected again by the beam splitter 16, passes through the relay lens 18, the relay lens 19 and then the image forming lens 22 thereby form an image on the photo-detector 23. If the eye E has a refractive error, the motor 58 is driven so as to move the target plate 13 along with the movable lens 21 to a conjugate position with the fundus of the eye E in accordance with a receive signal responsive to reflected light from the fundus received by the photo-detector 23.

Next, the first relay lens 32 is moved so as to place the fixation target 34 and the fundus of the eye E at conjugate positions with each other, and further moves the first relay lens 32 so that the adequate amount of diopter is to be fogged. With the eye E being fogged, the light sources 11, the corneal reflection eliminating mask 20 and the photo-detector 23 are made to be rotated 180° about the optical axis. During the rotation, the target plate 13 and the movable lens 21 move in response to the signal from the photo-detector 23. The potentiometer 60 detects the amount of the movement and thereby obtains a value of a refractive power in each meridian direction. The control circuit 50 gives a predetermined process to the obtained refractive power so as to obtain values of S (spherical power), C (cylindrical power) and A (cylindrical axial angle). For this measurement method of an eye refractive power, see U.S. Pat. No. 5,500,697 corresponding to Japanese Patent Publication of unexamined patent application No. HEI 7-39517 by the present applicant.

The control circuit 50 also obtains the pupil diameter (or the pupil area) from the signals processed in the aforementioned way by the image processing analyzing circuit 53 at the time of measuring the refractive power of the eye. The obtained information about the pupil diameter size is stored into the memory 62 along with the measurement result.

Such measurement as described above is repeated a plurality of times on one and the same eye to be examined and obtains the measurement results (it may be programmed to repeat the measurement while the measurement starting switch 6 is being depressed until a predetermined number of measurement results, exclusive of measurement errors, are obtained).

When a predetermined number of the measurement results are obtained (or when the print switch is depressed), the control circuit 50 compares the values indicative of the pupil sizes stored in the memory 62, and thereby selects the eye refractive power measured at the time the pupil size is the greatest as the typical value. It is said about a human eye that when a pupil of an eye is smaller in the same surroundings, the eye is effected by accommodation. In other words, when the pupil expands, eye accommodation is less effective. Thus, when intended to select the typical value among the plurality of measurement results, it is assumed that the eye refractive power which is measured at the time the pupil size is the greatest secures the highest accuracy. Especially, in the case of an eye having low hyperopia, the accommodation is unstable and hence the pupil changes in size frequently during a plurality of measurements. In this case, if the median or the average is taken as the typical value, the result may indicate the myopic refractive power. On the contrary, if the measured value at the time where the pupil size is the greatest is taken as the typical value, the possibility of leading such values is greatly reduced. Being able to decide the typical value accurately allows a subjective refractive power measurement following to the first measurement to be performed properly.

The typical value decided in the aforementioned way will be printed out from the printer 63 along with the results of the plurality of refractive power measurements. The pupil sizes may be printed out in correspondence with each measurement result.

If an external device such as a subjective refractive power measurement apparatus 80 or the like is connected, the typical value decided in the aforementioned way will be transferred to the same. In the subjective refractive power measurement, an initial optical element will be selected and arranged based on this typical value, which allows to perform the measurement accurately and speedily.

In the preferred embodiment as described above, the pupil size obtained along with the refractive power in the same measurement is utilized in the way to decide the typical value of the plurality of refractive power measurement results by selecting one measurement result. In stead of utilizing the changes in the pupil size to decide the typical value, this may be applied to how to detect an eye having low hyperopia. This is to take advantage of the characteristic that low hyperopia is easily effected by accommodation (the pupil size changes easily). Therefore, based on the amount of the changes in the pupil size in the plurality of measurements, possibility that the eye may have low hyperopia can be detected. When the possibility is recognized, the result is to be displayed along with the measured value (or the typical value). This allows the examiner to be aware of the possibility that the eye may have low hyperopia when proceeding to the next step of the measurement.

In the embodiment, the pupil size is utilized to decide the typical value of the plurality of measurement results; the measurement result with the greatest pupil size, which is measured at the same time of measuring the refractive power, is selected to be the typical value. It is also possible to utilize the pupil size in order to eliminate the refractive power measured at the time where the eye is effected by accommodation (the pupil size is small). That is to say, if the pupil detection results indicate the pupil being smaller than the predetermined pupil size, the corresponding refractive power measurement results are eliminated from the plurality of the measurement results. The typical value will be decided from the remaining measurement results. If the only one measurement result remains, the same will be the typical value. If plurality of the measurement results remain, the median or the average of the remaining measurement results will be the typical value. If no measurement result remains (all the pupil detection results indicate that the pupil size is smaller than the predetermined pupil size), another measurement should be performed again. It will be suitable to make an arrangement so that the examiner can arbitrarily change the predetermined pupil size.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An eye refractive power measurement apparatus including refractive power measurement means for objectively measuring a refractive power of an eye to be examined based on reflected light from a fundus of the eye, the apparatus comprising:

pupil detecting means for detecting a pupil size upon measuring the refractive power of the eye by said refractive power measurement means;

memory means for storing plurality of refractive power measurement results obtained by said measurement means and pupil detection results obtained by said pupil detecting means in correspondence therebetween;

typical value determination means for determining a typical value of the refractive power based on the refractive power measurement results and the pupil detection results stored in said memory means; and output means for outputting the typical value determined by said typical value determination means.

2. The eye refractive power measurement apparatus according to claim 1, wherein said typical value determination means determines the typical value by selecting a refractive power measurement result corresponding to a greatest pupil size stored in said memory means.

3. The eye refractive power measurement apparatus according to claim 1, further comprising photographing means for photographing an anterior part of the eye, and wherein said pupil detecting means detects the pupil size based on output signals from said photographing means.

4. The eye refractive power measurement apparatus according to claim 1, wherein said pupil detecting means includes means for detecting either a pupil diameter or a pupil area.

5. The eye refractive power measurement apparatus according to claim 1, further comprising:

judging means for judging whether or not the eye possibly has low hyperopia based on the pupil detection results stored in said memory means; and display means for displaying a judgement result made by said judging means.

6. The eye refractive power measurement apparatus according to claim 1, wherein said typical value output by said output means is utilized as data for setting an initial value for a corrective optical system in subjective refractive power measurement.

7. The eye refractive power measurement apparatus according to claim 1, further comprising transmitting means for transmitting said typical value output by said output means to a subjective refractive power measurement apparatus.

8. An eye refractive power measurement apparatus comprising:

refractive power measurement means for objectively measuring a refractive power of an eye to be examined based on reflected light from a fundus of the eye;

pupil detecting means for detecting a pupil size upon measuring the refractive power of the eye by said refractive power measurement means;

memory means for storing plurality of refractive power measurement results obtained by said measurement means and pupil detection results obtained by said pupil detecting means in correspondence therebetween;

judging means for judging whether or not the eye possibly has low hyperopia based on the pupil detection results stored in said memory means; and display means for displaying a judgment result made by said judging means.

9. The eye refractive power measurement apparatus according to claim 8, wherein said judging means judges whether or not the eye possibly has low hyperopia based on change of the pupil size in the pupil detection results stored in said memory means.

10. An eye refractive power measurement apparatus comprising:

refractive power measurement means for objectively measuring a refractive power of an eye to be examined based on reflected light from a fundus of the eye;

pupil detecting means for detecting a pupil size upon measuring the refractive power of the eye by said refractive power measurement means;

memory means for storing plurality of refractive power measurement results obtained by said measurement means and pupil detection results obtained by said pupil detecting means in correspondence therebetween;

eliminating means for eliminating refractive power measurement results corresponding to pupil detection results in which the pupil size is smaller than a predetermined pupil size from the refractive power measurement results stored in said memory means;

typical value determination means for determining a typical value of the refractive power based on refractive power measurement results exclusive of the refractive power measurement results eliminated by said eliminating means; and output means for outputting the typical value determined by said typical value determination means.

11. The eye refractive power measurement apparatus according to claim 10, further comprising changing means with which an examiner can arbitrarily change said predetermined pupil size.

12. The eye refractive power measurement apparatus according to claim 10, wherein said typical value determination means obtains a median or an average of the refractive power measurement results exclusive of the refractive power measurement results eliminated by said eliminating means so as to determine said typical value by selecting said median or said average.

* * * * *